United States Patent
Vecchio et al.

(10) Patent No.: US 9,273,063 B2
(45) Date of Patent: Mar. 1, 2016

(54) METHOD FOR PREPARING A RIFAXIMIN PRODUCT

(71) Applicants: Emilio Vecchio, Cernusco sul Naviglio (IT); Roberta Pizzocaro, Milan (IT)

(72) Inventors: Emilio Vecchio, Cernusco sul Naviglio (IT); Roberta Pizzocaro, Milan (IT)

(73) Assignee: Salix Pharmaceuticals, Inc., Bridgewater, NJ (US)

( * ) Notice: Subject to any disclaimer, the term of this patent is extended or adjusted under 35 U.S.C. 154(b) by 0 days.

(21) Appl. No.: 14/261,138

(22) Filed: Apr. 24, 2014

(65) Prior Publication Data
US 2015/0011750 A1  Jan. 8, 2015

Related U.S. Application Data

(63) Continuation of application No. 13/970,576, filed on Aug. 19, 2013, now abandoned, which is a continuation of application No. 12/452,152, filed as application No. PCT/IB2008/052396 on Jun. 18, 2008, now abandoned.

(30) Foreign Application Priority Data

Jun. 20, 2007 (IT) .............................. MI2007A1241

(51) Int. Cl.
*C07D 498/22* (2006.01)
*C07D 491/22* (2006.01)

(52) U.S. Cl.
CPC ............ *C07D 491/22* (2013.01); *C07D 498/22* (2013.01)

(58) Field of Classification Search
CPC .................................................... C07D 498/22
See application file for complete search history.

(56) References Cited

U.S. PATENT DOCUMENTS 7,709,634 B2 * 5/2010 Kothakonda et al. ......... 540/456

* cited by examiner

*Primary Examiner* — Bruck Kifle
(74) *Attorney, Agent, or Firm* — Toan P. Vo; Bass Berry & Sims PLC; Janelle D. Waack

(57) ABSTRACT

A process is described which enables Rifaximin in a completely amorphous form to be obtained. Said process comprises the steps of dissolving crude Rifaximin in absolute ethanol while hot and then collecting after precipitation by—cooling the title compound under amorphous form.

20 Claims, 4 Drawing Sheets

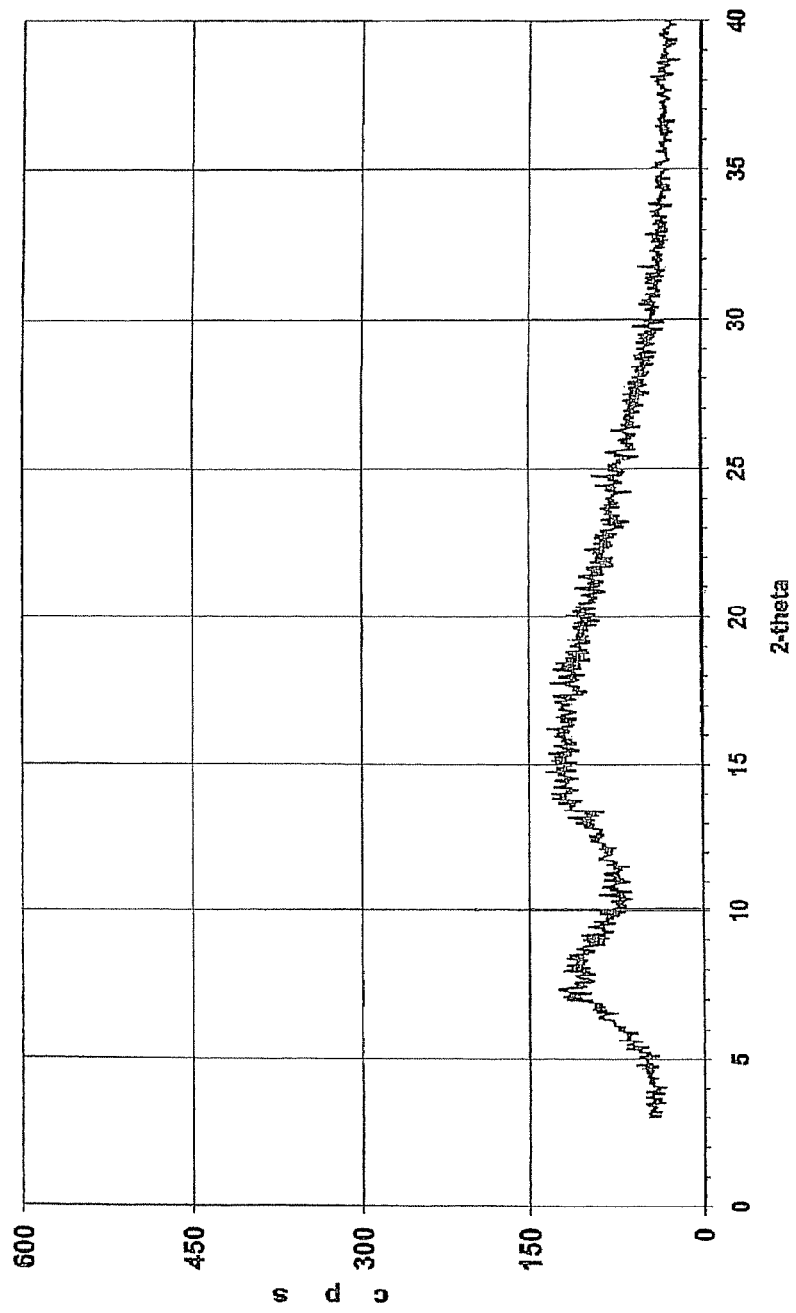

METHOD FOR PREPARING A RIFAXIMIN PRODUCT

FIELD OF THE INVENTION

The present invention relates to the preparation of Rifaximin in amorphous form.

STATE OF THE ART

As is known Rifaximin is a non-systemic antibiotic belonging to the rifaximin-family, applied in the treatment of various pathologies including in particular diarrhea caused by E. coli or irritable bowel syndrome.

Various polymorphic forms of the product are known, for which various synthesis and purification processes have been described.

The present invention instead relates to the preparation of Rifaximin in amorphous form, by a process that comprises precipitating the desired product in absolute ethanol starting from a solution of crude Rifaximin.

Pharmaceutical active principles in amorphous form are in general more soluble than the corresponding crystalline forms, and this can present advantages—in terms—of improved absorption per os and consequently improved bioavailability.

DETAILED DESCRIPTION OF THE INVENTION

The process of the invention uses as starting product crude Rifaximin containing water.

The starting product is dissolved in absolute ethanol in the presence of ascorbic acid and the solution subjected to mild heating with stirring; the product precipitates by cooling the solution while stirring, and is then collected by filtration, washed with cold absolute ethanol and dried under vacuum.

The absence of significant peaks in the PXRD spectra carried out on the product obtained in this manner is evidence of the purity of the amorphous product obtained.

Example 1

20 g of crude rifaximin (containing an average water quantity of between 4 and 7%) were placed in a reaction flask in which 0.2 g of ascorbic acid and 200 ml of absolute ethanol were added. The suspension was heated to 60° C. with stirring until completely dissolved. The solution was allowed to cool to 25° C., maintaining stirring for a further three hours.

After precipitation, the suspension was left for a further 2 hours with stirring at a temperature of 12° C., then filtered.

The product on the filter was washed with 20 ml of cold absolute ethanol and the wet solid dried under vacuum at 70° C. for 18 hours until a KF value less than 4% was attained.

15 g of pure amorphous rifaximin were obtained.

Figure 1:
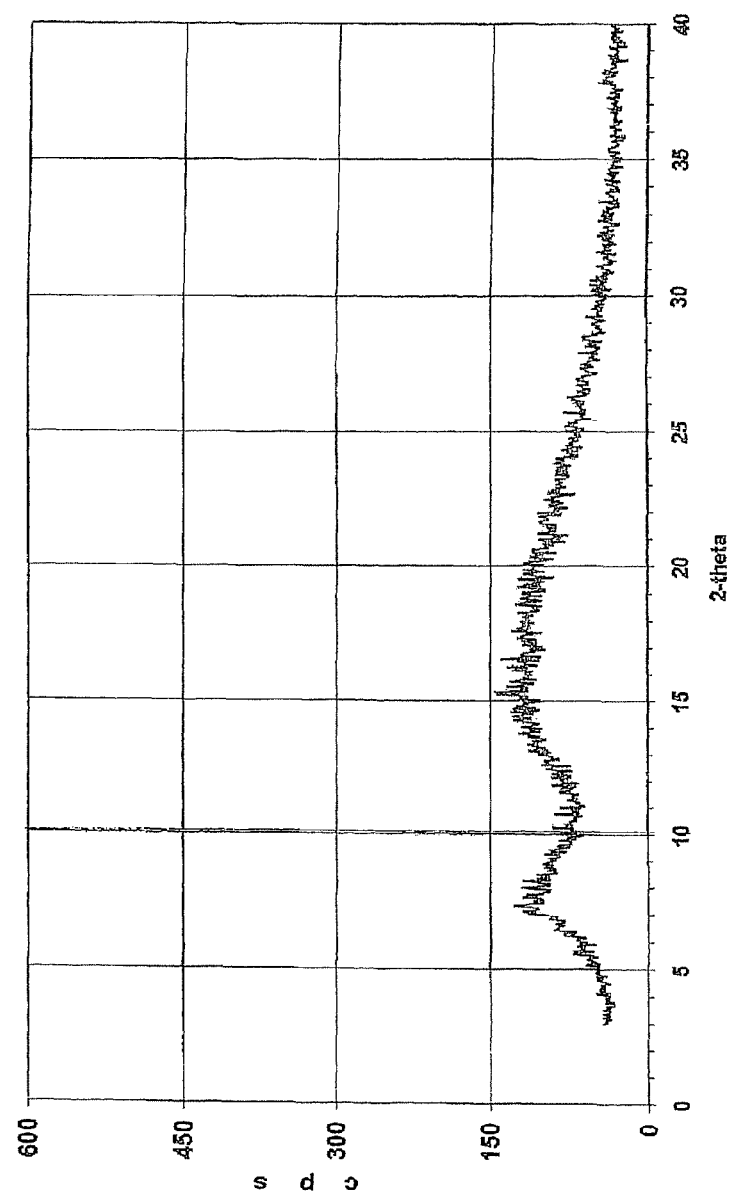
FIG. 1(a and b) and FIG. 2(a and b) show respectively the PXRD and IR spectra of rifaximin obtained according to the process of the present invention.
Figure 2A:
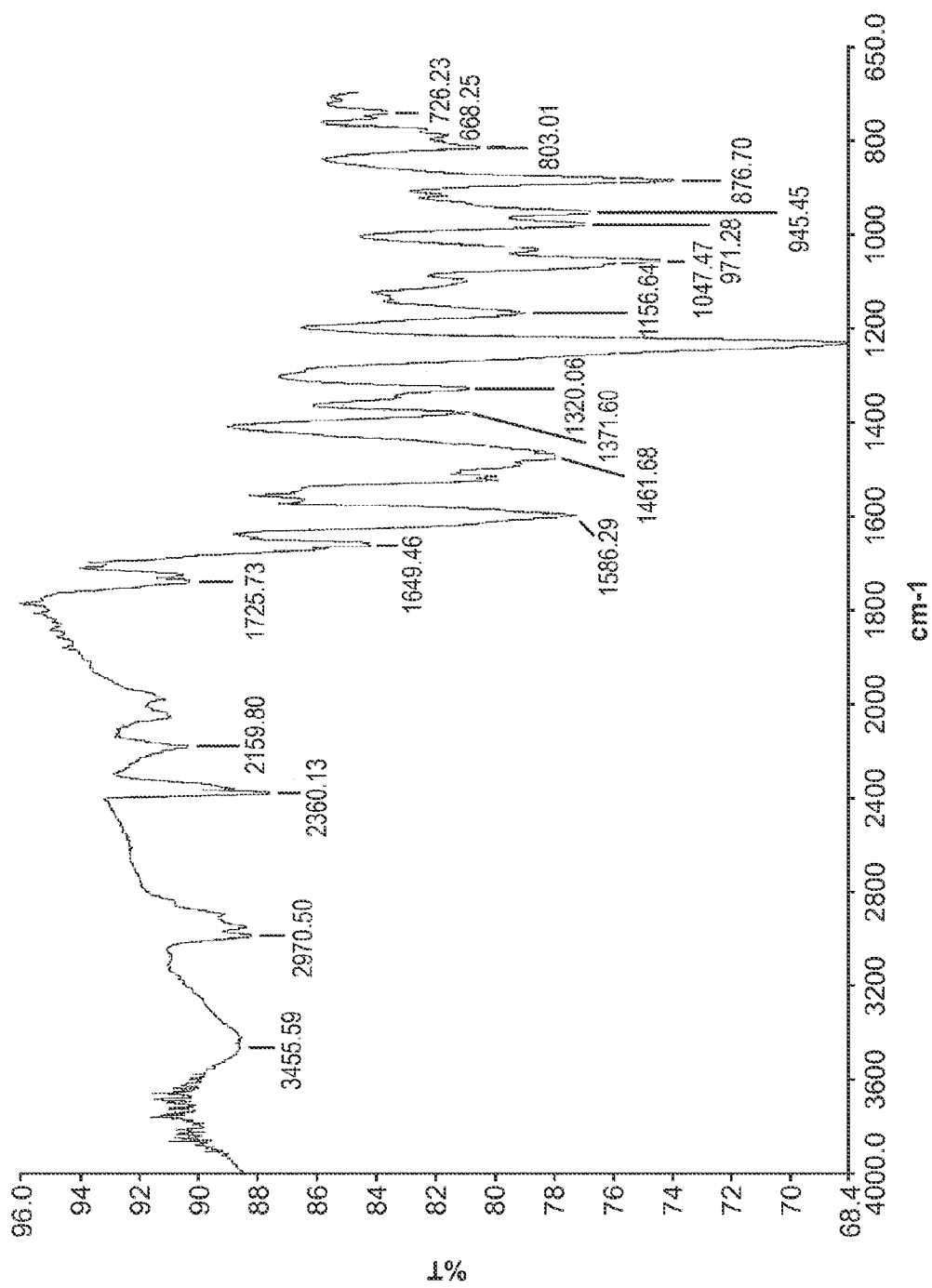

The PXRD and IR spectra of the obtained product are shown in FIGS. 1a and 2a respectively.

Example 2

20 g of crude rifaximin (containing an average quantity of water of between 4 and 7%) were placed in a reaction flask in which 0.2 g of ascorbic acid and 200 ml of absolute ethanol were added. The suspension was heated to 40° C. with stirring until completely dissolved. The solution was allowed to cool to 18° C., maintaining stirring for a further three hours.

After precipitation the suspension was left for a further 2 hours with stirring at a temperature of 8° C., then filtered.

The product on the filter was washed with 20 ml of cold absolute ethanol and the wet solid dried under vacuum at 60° C. for 18 hours until a KF value less than 4% was attained.

14 g of pure amorphous rifaximin were obtained.

Figure 2B:
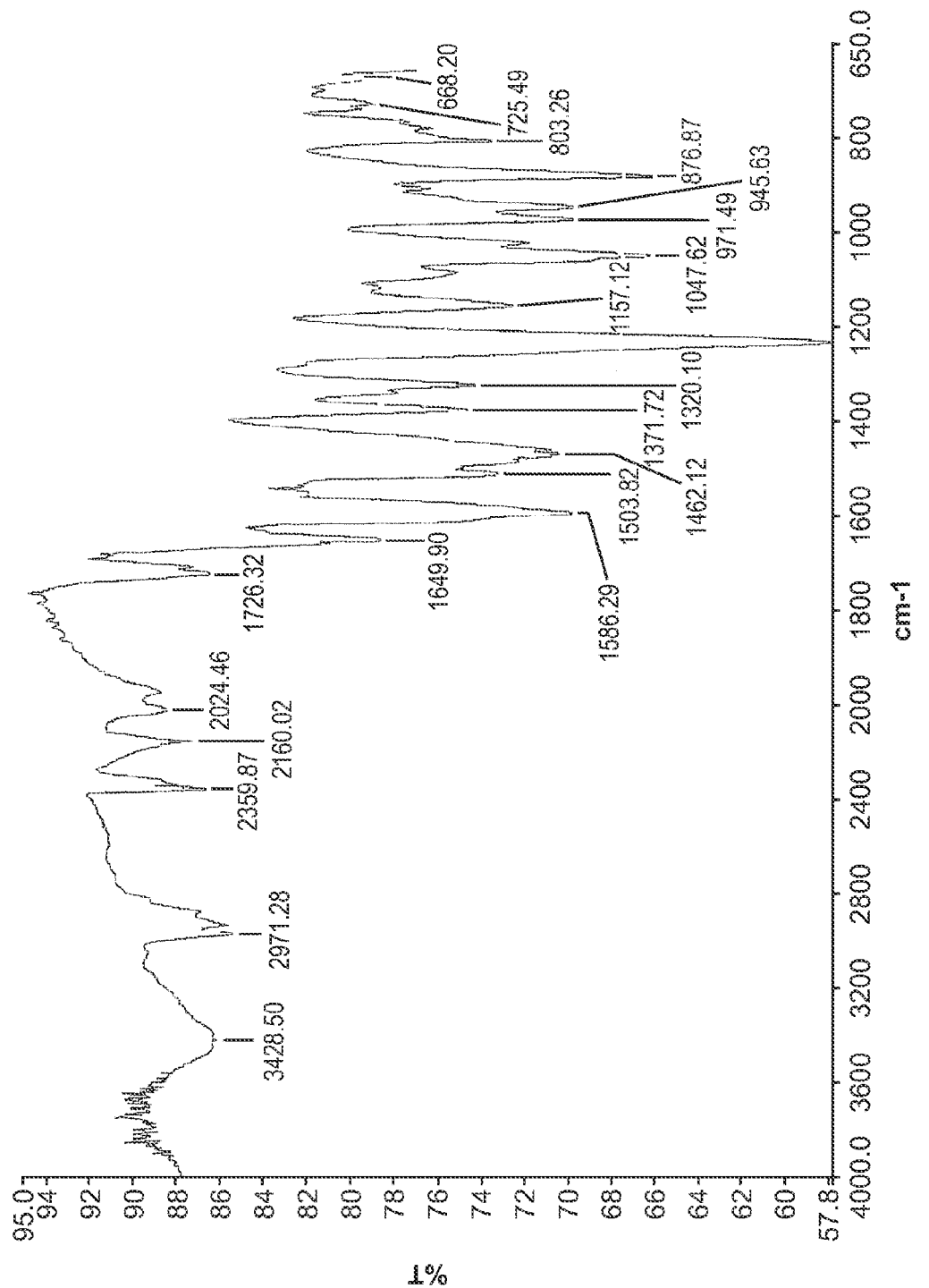

The PXRD and IR spectra of the obtained product are shown in FIGS. 1b and 2b respectively.

The dissolution profile of the substance in amorphous form was also determined, and compared with that of the substance in crystalline form.

It was found that the amorphous form easily dissolves in ethanol even without stirring, while the crystalline form is less wettable.

Moreover, with regard to water solubility, after conditioning a dissolution tester (Pharma Test Type PTW S III s/n 5390) using distilled water at a temperature of 37° C.±0.5° C. at a speed of 100 rpm, four dissolutions were carried out, in each of which the first three vessels of the dissolution tester were used for the substance in crystalline form and the last three for the substance in amorphous form.

10 ml of the solute were withdrawn from each vessel after 15 minutes of stirring; the withdrawn samples were filtered with 0.45 μm filters and subjected to spectophotometric analysis, repeating the operation after 30 and 60 minutes.

After one hour of dissolution, the substance in crystalline form has a concentration of dissolved substance equal to about 7% of that of the substance in amorphous form.

Consequently, the substance in amorphous form has a dissolved percentage which is one order of magnitude greater than that of the substance in crystalline form.

The invention claimed is:

1. A method for preparing a rifaximin product comprising:
   (a) dissolving crude rifaximin in heated absolute ethanol;
   (b) precipitating the rifaximin by cooling the solution, without the addition of antisolvent;
   (c) collecting the solid by filtering and washing; and
   (d) drying the solid.

2. The method according to claim 1, wherein the solution in step (b) is cooled to 8-25° C.

3. The method according to claim 2, wherein the solution in step (a) is heated to 40-60° C.

4. The method according to claim 3, wherein the solid in step (d) is dried under vacuum at 60-70° C.

5. The method according to claim 3, wherein the solid in step (d) is dried until the solid attains a KF value of less than 4%.

6. The method according to claim 5, wherein the crude rifaximin in step (a) is dissolved in absolute ethanol in the presence of ascorbic acid.

7. The method according to claim 6, wherein the crude rifaximin has a water content of between 4 and 7%.

8. A method for preparing a rifaximin product comprising:
   (a) dissolving crude rifaximin in a heated solvent selected from $C_1$ to $C_4$ alcohols;
   (b) precipitating the rifaximin by cooling the solution, without the addition of antisolvent;
   (c) collecting the solid by filtering and washing; and
   (d) drying the solid.

9. The method according to claim 8, wherein the solution in step (b) is cooled to 8-25° C.

10. The method according to claim 9, wherein the solution in step (a) is heated to 40-60° C.

11. The method according to claim 10, wherein the solid in step (d) is dried under vacuum at 60-70° C.

12. The method according to claim 10, wherein the solid in step (d) is dried until solid attains a KF value of less than 4%.

13. The method according to claim 12, wherein the crude rifaximin in step (a) is dissolved in absolute ethanol in the presence of ascorbic acid.

14. The method according to claim 13, wherein the crude rifaximin has a water content of between 4 and 7%.

15. A method for preparing a rifaximin product comprising:
   (a) dissolving crude rifaximin in absolute ethanol heated to 40-60° C.;
   (b) precipitating the rifaximin by allowing the solution to cool to 18-25° C. and stirring for three hours;
   (c) further cooling the solution to 8-12° C. and stirring for two hours;
   (d) collecting the solid by filtering and washing; and
   (e) drying the solid.

16. The method according to claim 15, wherein the solid in step (e) is dried under vacuum at 60-70° C.

17. The method according to claim 16, wherein the solid in step (e) is dried until the solid attained a KF value of less than 4%.

18. The method according to claim 17, wherein the crude rifaximin has a water content of between 4 and 7%.

19. The method according to claim 18, wherein the crude rifaximin is dissolved in absolute ethanol in the presence of ascorbic acid.

20. The method according to claim 19, wherein the crude rifaximin in step (a) is dissolved in approximately 10 milliliters of absolute ethanol per gram of crude rifaximin.

\* \* \* \* \*